US00PP32343P2

(12) United States Plant Patent
Hansen

(10) Patent No.: US PP32,343 P2
(45) Date of Patent: Oct. 13, 2020

(54) ***SALVIA* PLANT NAMED 'LILAC LIPSTICK'**

(50) Latin Name: ***Salvia pratensis* hybrid**
Varietal Denomination: Lilac Lipstick

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/873,094

(22) Filed: Jan. 30, 2020

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./475
See application file for complete search history.

*Primary Examiner* — Susan McCormick Ewoldt

(57) ABSTRACT

The new and distinct cultivar of perennial *Salvia* plant named 'Lilac Lipstick' characterized by its large, lilac-pink flowers from dark mauve buds and calyxes, densely arranged in verticils. The new plant has a medium height, compact, rounded habit with stiff, upright, heavily-branched stems and a strong vigorous growth rate and dark gray-green foliage. 'Lilac Lipstick' is useful for landscaping as a specimen plant or en masse.

1 Drawing Sheet

Botanical denomination: *Salvia pratensis* hybrid.
Cultivar designation: 'Lilac Lipstick'.

STATEMENT REGARDING PRIOR DISCLOSURES UNDER 37 CFR 1.77(B)(6)

The first public disclosure of the new plant, in the form of a photograph and brief description on a website operated by Walters Gardens, Inc. on Feb. 1, 2019. Subsequently, the new plant was advertised in the "Walters Gardens 19-20 Catalog" first distributed on May 29, 2019. The claimed plant was first sold on Jul. 29, 2019 by Walters Gardens, Inc., who obtained the plant and all information relating thereto, from the inventor. Walters Gardens, Inc. obtained the new plant and all information on the new plant from the inventor. No plants of *Salvia* 'Lilac Lipstick' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of ornamental sage plant hereinafter referred to by the cultivar name *Salvia* 'Lilac Lipstick' or as the new plant. The new plant was selected from an insect pollination in late spring of 2014 with 'Midnight Model' U.S. Plant Pat. No. 29,498 as the female or seed parent and the male parent is 13-10-x (not patented) at a wholesale perennial nursery in Zeeland, Mich., USA. Seed was collected in the summer of 2014 and sown at the same nursery. The new plant was initially evaluated in the summer of 2016 and assigned the breeder code 14-1-2 through the trial process prior to assigning the cultivar name.

The new *Salvia* was further evaluated and asexually propagated initially by division and later by basal cuttings taken at the same nursery in Zeeland, Mich., USA in 2016. Evaluation of these and further cutting grown plants shows that *Salvia* 'Lilac Lipstick' continues to be stable and produce true to type plants in successive generations of asexual propagation.

SUMMARY OF THE INVENTION

Plants of *Salvia* 'Lilac Lipstick' have not been observed under all possible environmental conditions. The phenotype may vary somewhat with variations in environment such as temperature, nutrition and light intensity without, however, any variance in genotype.

*Salvia* 'Lilac Lipstick' can be closely compared to *Salvia* 'Midnight Model' U.S. Plant Pat. No. 29,498, 'Ballerina Pink' U.S. Plant Pat. No. 29,957, 'Pretty in Pink' U.S. Plant Pat. No. 29,550, 'Pink Dawn' U.S. Plant Pat. No. 26,343, 'Moulin Rouge' copending U.S. Plant patent application Ser. No. 16/873,095 and 'Sweet Petite' U.S. Plant Pat. No. 31,285. 'Midnight Model' has flowers that are violet-blue on slightly taller plants. 'Ballerina Pink', a sister sibling to the female parent, has soft pink flowers and dark mauve calyces on plants just slightly taller. 'Pretty in Pink', another sister sibling to the female parent, has flowers that are vibrant lavender-pink with darker pink calyxes and slightly taller habit. 'Pink Dawn' has a cotton candy pink flowers that is less two-tone. 'Moulin Rouge' has flowers that are deep rosy-pink with less contrasting two-tone effect. 'Sweet Petite' has slightly shorter habit and flowers of lavender-pink with dark rose buds. Comparison with the male parent is not possible as it was not maintained.

The following characteristics in combination distinguish *Saliva* 'Lilac Lipstick' as a new and distinct cultivar from all other cultivars known to the inventor:

1. Large, lilac pink flowers with a lighter shade on the top petal and darker shade on the lower petal densely arranged in verticils;
2. Stiff, upright, heavily-branched stems;
3. Dark mauve flower buds;

4. Medium height, compact, rounded, strong, vigorous and winter-hardy habit;
5. Rugose, dark, gray-green foliage.

BRIEF DESCRIPTION OF THE DRAWINGS

The photographs of the new plant demonstrate the unique traits and the overall appearance of *Salvia* 'Lilac Lipstick'. The colors are as accurate as reasonably possible with color reproductions. Variation in ambient light spectrum, source and direction may cause the appearance of minor variation in color. The plant used in the photographs was a two-year old plant grown in an open, full-sun trial garden at a wholesale perennial nursery in Zeeland, Mich. with supplemental water and fertilizer when needed.

DETAILED BOTANICAL DESCRIPTION

Figure 1:
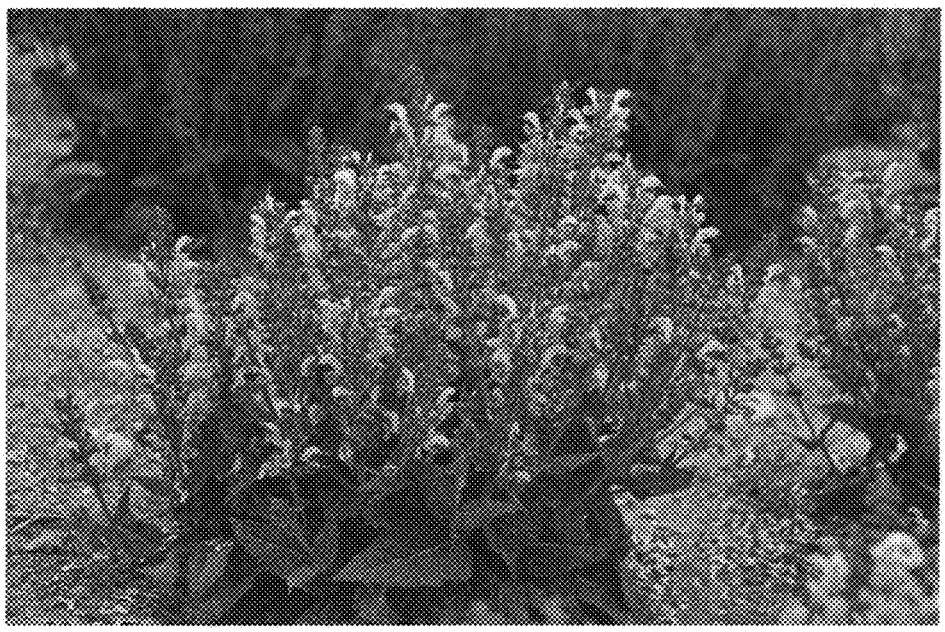
FIG. 1 shows the plant habit in full flower in a landscape.
Figure 2:
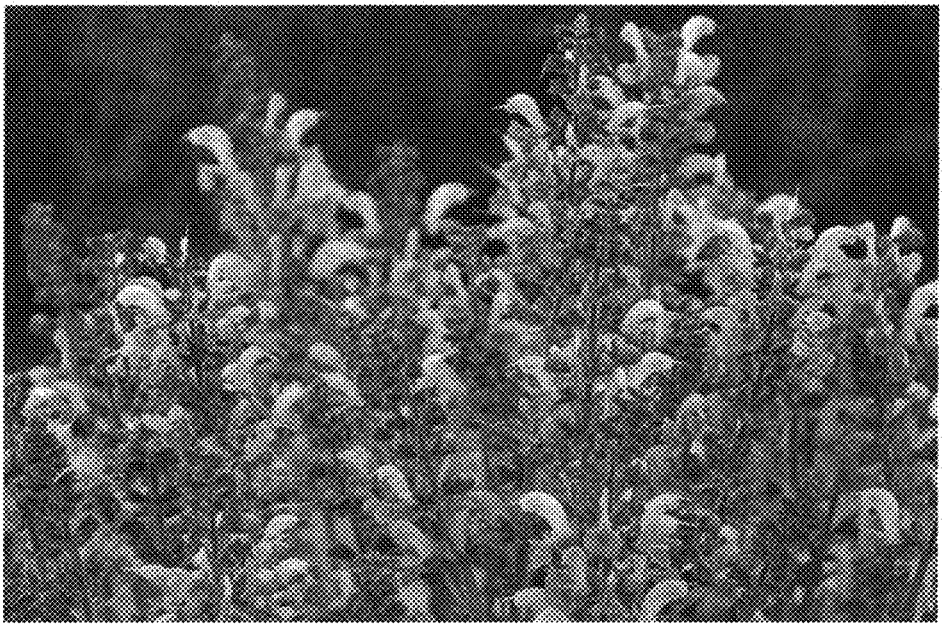
FIG. 2 shows a close-up of the flower scape with the buds, flowers, stems and calyxes.

The following descriptions and color references except where common dictionary terms are used are based on the 2015 edition of The Royal Horticultural Society Colour Chart. *Salvia* 'Lilac Lipstick' has not been observed under all possible environments. The phenotype may vary slightly with different growing environments such as temperature, light, fertility, soil pH, moisture and plant maturity levels, but without any change in the genotype. The following observations and size descriptions are based on two-year old plants growing in an outdoor full-sun trial garden and greenhouse-forced two-year-old plants at a wholesale perennial nursery in Zeeland, Mich. Plants were given supplemental water and fertilizer. Plant growth regulators were used for the greenhouse trials only.

Botanical classification: *Salvia pratensis* hybrid;

Parentage: Female or seed is 'Midnight Model'; male or pollen parent is 13-10-x;

Plant habit: Winter-hardy herbaceous perennial; multi-stemmed, compact, rounded, with mostly basal foliage, and flowers in several tightly arranged verticils on branched upright racemes displayed above foliage; in flower with panicles about 40 cm tall and about 47 cm wide at the fullest point; cauline foliage extends up the stems about 25 cm; about 17 flowering panicles per plant;

Propagation: By basal vegetative shoot cuttings; time to produce a rooted stems about two weeks;

Growth rate: Rapid, vigorous, finishing in a 65 mm container in about 7 weeks from rooted cutting, and from 65 mm container to flowering 3.8 liter container in about 8 weeks Root description: Fine, well-branched; color dependent on age and soil type, from cream to dark tan in color;

Foliage: Opposite; simple; slightly rugose; lanceolate; margin irregularly crenate and sparsely ciliolate; adaxial surface glabrous, and abaxial puberulent; acute apex and base cordate; leaf blades to about 14.5 cm long and 7.4 cm across, decreasing in size distally; average about 13.3 cm long and 5.8 cm across; faint sage fragrance;

Foliage color: Young adaxial surface nearest RHS 138A, young abaxial surface nearest RHS 137B; mature adaxial nearest NN137A, mature abaxial nearest RHS 137B;

Venation: Reticulate; impressed on adaxial side and costate on abaxial side; pubescent adaxial and abaxial;

Vein color: Adaxial midrib between RHS 196A and RHS 196B; adaxial primary and secondary veins nearest RHS N148C toward midrib and distally nearest RHS NN137A; abaxial midrib nearest RHS 145C; abaxial primary and secondary veins nearest RHS 145B near center and distally nearest RHS 148D toward leaf margin;

Petiole: Concavo-convex; puberulent adaxial and abaxial and ciliolate margin; to about 8.0 cm long and 9.0 mm wide at base decreasing distally, average 6.0 cm long and 7.0 mm wide at base;

Petiole color: Adaxial and abaxial center between RHS 147C and RHS 147D, marginally nearest RHS 137B, basal 8mm strongly blushed to solid nearest RHS 185D;

Flower description: Perfect; bilabiate; zygomorphic; fused corolla portion glabrous adaxial and puberulent abaxial;

Flower size: 23.0 mm long to tip of exserted stigma, 13.0 mm tall, 5.0 mm wide; corolla 22.0 mm long, 19.0 mm tall; corolla fused basal portion 8.0 mm long, 6.0 mm tall and 3.0 mm wide;

Inflorescence: Panicle; branched at about 45° angle, rarely compound branched; branches to 18 cm long and 3.0 mm across base; flowering portion 33 cm tall and 23 cm across; verticillate with flowering generally beginning at lower verticils and advancing up the scape, but not all flowers at each verticil opening at the same time giving the effect of a scape being in continuous flower for longer periods; typically six flowers per verticil; average distance between verticils about 10.0 mm, greater proximally and less distally; about 15 verticils per plant; about 150 to 250 flowers per panicle;

Flowering period: Flowering beginning late spring for about six weeks and repeating if initial inflorescences removed;

Peduncle: Quadrangular; pubescent to glandular; to 36.0 mm long and 4.0 mm across below flowers;

Peduncle color: Proximal portion nearest RHS 138A and distal portion nearest RHS 187A;

Flower attitude: Mostly horizontal;

Flower longevity: About four days on the plant or as cut flower; self-cleaning, petals not persistent;

Flower fragrance: None detected under present growing conditions;

Flower buds one day prior to anthesis: Obovoid; arcuate dorsally, flat ventrally and flattened slightly laterally; with rounded apex; pubescent; about 14.0 mm long, 5.0 mm tall and 3.0 mm wide;

Bud color: Exposed petals blend between RHS 71A and RHS 187D; abaxial calyx nearest RHS 187A;

Petals: Bilabiate corolla; upper hood lip and lower lip (labium) with three lobes; glandular abaxial and glabrous adaxial;

Hood (upper) petal: Glandular abaxial, glabrous adaxial; about 19.0 mm long, 9.0 mm tall and 2.0 mm across; folded along longitudinal axis; apex rounded and emarginate, with 1 mm deep notched apex and base fused with labium in proximal 9.0 mm;

Hood color: Adaxial nearest RHS 77D with basal 6 mm nearest RHS NN155D, abaxial nearest RHS N74D proximally with distal 3 mm nearest RHS N78B and basal 6 mm nearest RHS NN155D;

Labium (lower) petal: Consisting of three lobes, two proximal side lobes and larger center lobe; side lobes glabrous adaxial and puberulent abaxial, center lobe glandular abaxial base and glabrous abaxial margins and distally, adaxial glabrous;

*Center lobe.*—Obcordate; folded along longitudinal axis; truncate emarginate apex with notch about 1.0 mm deep; margin serrate to erose; size about 15.0 mm long (including fuse base) extending 6 mm beyond fusion point; natural width 3.0 mm and when spread to 5.0 mm.

*Center lobe color*.—Adaxial base nearest RHS NN155D, distally nearest RHS 77A; abaxial base nearest RHS NN155D, just outside calyx nearest RHS 77B, center nearest RHS 76B and distally nearest RHS 77A.

*Side lobes*.—Lanceolate; adpressed to center lobe; apices acute; base fused to corolla tube; slightly revolute; size about 5.0 mm long from fusion and 1.5 mm wide.

*Side lobes color*.—Nearest RHS 77A adaxial, abaxial between RHS 77A and RHS N81B.

Androecium: Two; fused with labium, contained within hood petal except when triggered by pollinator;

*Filament*.—Glabrous, fused about 9.0 mm from base of labium petal; arcuate around inside of hood petal; about 13.0 mm long and less than 0.3 mm diameter with a 1.0 mm long trip mechanism longitudinally folded at base; color of filament between RHS 75C and RHS 75D; color of trip mechanism between RHS 75C and RHS 75D.

*Anther*.—Glabrous; oblong ellipsoidal; dorsifixed; longitudinal; about 2.0 mm long and 1.0 mm diameter; color nearest RHS N187A.

*Pollen*.—Abundant; less than 0.1 mm circumference; color nearest RHS 12A.

Gynoecium: One, arcuate around inside of hood petal;

*Style*.—Exserted; about 25.0 mm long and 0.5 mm diameter; color nearest RHS NN155D at base, transitioning distally to nearest RHS N78D.

*Stigma*.—Bifurcate and curved in the terminal 1.5 mm; about 0.2 mm diameter; apex acute; color nearest RHS 77A.

*Ovary*.—Superior; four seeded; color between RHS N163D and RHS 163B.

Fruit: Nutlet, one to four per flower; globose; about 1.5 mm diameter; color darker than RHS 200A;

Calyx: Campanulate; fused in basal 5.0 mm; tube about 10.0 mm long and 7.0 mm tall at mouth and 4.5 mm wide; lower set bifurcate in distal 3.5 mm; upper set of trifurcate slightly folded in middle in distal 2.0 mm; glandular abaxial and glabrous adaxial;

Sepals: Five, three upper and two lower; linear; acute apex; 10.0 mm long, 1.5 mm across at fusion and fused in basal 5.0 mm;

Sepal color: Variable depending on light intensity; adaxial proximal 3 mm nearest RHS 137C with veins nearest RHS 137C, distal portion nearest RHS 138A; low light abaxial nearest RHS 187A to RHS 146D in low light, with veins of nearest RHS146A to RHS 187A in high light;

Bracts: Each verticil and branch subtended by two opposite deltoid bracts; apex narrowly acute to acuminate, base sessile and truncate, margin crenate; glabrous adaxial and pubescent abaxial; bract size up to 24.0 mm long and 15.0 mm wide, decreasing distally;

Bract color: Variable with light intensity, in lower light adaxial surfaces between RHS 137A and RHS NN37A with midrib nearest RHS 145D, abaxial nearest RHS NN137C with midrib of nearest RHS 145D; color with more intense light exposure between RHS N92A and RHS N92B on both surfaces;

Pedicels: Cylindrical; puberulent to glandular; about 2.0 to 4.0 mm long and 1.0 mm diameter; curving outwardly;

Pedicel color: Nearest RHS 145A in proximal portion of peduncle and RHS 187A distally;

Culture: Plants of *Salvia* 'Lilac Lipstick' perform best with adequate moisture and good drainage and are hardy from USDA zone 3 to 8.

Disease and pest resistance: Resistant to diseases and pests beyond that common to *Salvia* has not been noted.

It is claimed:

1. The new and distinct perennial *Salvia* plant named 'Lilac Lipstick' as herein described and illustrated.

* * * * *